United States Patent
Flynn et al.

(10) Patent No.: US 10,412,515 B2
(45) Date of Patent: Sep. 10, 2019

(54) FITTING OF HEARING DEVICES

(71) Applicants: Mark Flynn, Gothenburg (SE); Bjorn Davidsson, Gothenburg (SE)

(72) Inventors: Mark Flynn, Gothenburg (SE); Bjorn Davidsson, Gothenburg (SE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 15/332,365

(22) Filed: Oct. 24, 2016

(65) Prior Publication Data

US 2017/0041723 A1    Feb. 9, 2017

Related U.S. Application Data

(63) Continuation of application No. 14/006,808, filed as application No. PCT/IB2012/051380 on Mar. 22, 2012, now Pat. No. 9,479,879.

(Continued)

(51) Int. Cl.
*H04R 29/00* (2006.01)
*H04R 25/00* (2006.01)
*A61B 5/12* (2006.01)

(52) U.S. Cl.
CPC ............. *H04R 25/70* (2013.01); *A61B 5/12* (2013.01); *H04R 25/30* (2013.01); *H04R 25/305* (2013.01);
(Continued)

(58) Field of Classification Search
CPC combination set(s) only.
See application file for complete search history.

(56) References Cited

U.S. PATENT DOCUMENTS 3,809,829 A    5/1974   Vignini et al.
4,498,461 A    2/1985   Hakansson
(Continued)

FOREIGN PATENT DOCUMENTS

EP    2066140 A1    6/2009
WO    9112783 A1    9/1991
(Continued)

OTHER PUBLICATIONS

F.M. Vaneecloo et al., "Rehabilitation prothetique B.A.H.A. des cophoses unilaterales," Annales D'oto-Laryngies et de Chirurgie Cervicofaciale, vol. 117, No. 6, Dec. 2000, pp. 410-417.
(Continued)

*Primary Examiner* — Amir H Etesam
(74) *Attorney, Agent, or Firm* — Pilloff Passino & Cosenza LLP; Martin J. Cosenza (57) ABSTRACT

The present invention relates to recipient fitting of a hearing device. An embodiment of the present invention determines the transmission loss for sound applied to the recipient by the hearing device. Separate gains are then determined for compensating for the determined transmission loss and the measured hearing loss of the recipient. For example, in an embodiment, the hearing device may compensate for transmission losses in a 1:1 manner (i.e., the transmission loss in 100% compensated for). The hearing device may apply a different gain to compensate for the hearing loss, such as a gain that is a fraction (e.g., 33-55%) of the measured hearing loss.

29 Claims, 6 Drawing Sheets

Related U.S. Application Data (60) Provisional application No. 61/466,832, filed on Mar. 23, 2011.

(52) U.S. Cl.
CPC ......... *H04R 25/356* (2013.01); *H04R 25/558* (2013.01); *H04R 25/606* (2013.01)

(56) References Cited

U.S. PATENT DOCUMENTS

| | | | |
|---|---|---|---|
| 4,776,322 A | 10/1988 | Hough et al. |
| 4,904,233 A | 2/1990 | Hakansson et al. |
| 4,982,434 A | 1/1991 | Lenhardt et al. |
| 5,197,332 A | 3/1993 | Shennib |
| 5,323,468 A | 6/1994 | Bottesch |
| 5,434,926 A | 7/1995 | Watanabe et al. |
| 5,800,475 A | 9/1998 | Jules |
| 5,805,571 A | 9/1998 | Zwan et al. |
| 5,879,283 A | 3/1999 | Adams et al. |
| 5,913,815 A | 6/1999 | Ball et al. |
| 5,991,419 A | 11/1999 | Brander |
| 6,094,489 A | 7/2000 | Ishige |
| 6,327,370 B1 | 12/2001 | Killion et al. |
| 6,496,585 B1 | 12/2002 | Margolis |
| 6,549,633 B1 | 4/2003 | Westermann |
| 6,602,202 B2 | 8/2003 | John et al. |
| 6,643,378 B2 | 11/2003 | Schumaier |
| 6,788,790 B1 | 9/2004 | Leysieffer |
| 6,840,908 B2 | 1/2005 | Edwards et al. |
| 6,895,345 B2 | 5/2005 | Bye et al. |
| 7,006,646 B1 | 2/2006 | Baechler |
| 7,018,342 B2 | 3/2006 | Harrison et al. |
| 7,068,793 B2 | 6/2006 | Shim |
| 7,074,222 B2 | 7/2006 | Westerkull |
| 7,526,958 B2 | 5/2009 | Nojima |
| 7,630,507 B2 | 12/2009 | Kates |
| 8,532,322 B2 | 9/2013 | Parker |
| 2002/0146137 A1 | 10/2002 | Kuhnel et al. |
| 2004/0028249 A1 | 2/2004 | Asnes |
| 2004/0028250 A1 | 2/2004 | Shim |
| 2004/0033962 A1 | 2/2004 | Tietze et al. |
| 2004/0078057 A1 | 4/2004 | Gibson |
| 2004/0082980 A1 | 4/2004 | Mouine et al. |
| 2004/0152946 A1 | 8/2004 | Franck |
| 2004/0204921 A1 | 10/2004 | Bye et al. |
| 2005/0078838 A1 | 4/2005 | Simon |
| 2005/0171579 A1 | 8/2005 | Tasche et al. |
| 2006/0018488 A1 | 1/2006 | Viala et al. |
| 2006/0115105 A1 | 6/2006 | Brumback et al. |
| 2006/0211910 A1 | 9/2006 | Westerkull |
| 2006/0287689 A1 | 12/2006 | Debruyne et al. |
| 2007/0019818 A1 | 1/2007 | Kurz |
| 2007/0135730 A1 | 6/2007 | Cromwell et al. |
| 2007/0223752 A1 | 9/2007 | Boretzki et al. |
| 2007/0261491 A1 | 11/2007 | Nojima |
| 2008/0212810 A1 | 9/2008 | Pedersen |
| 2008/0285781 A1 | 11/2008 | Aerts et al. |
| 2008/0292122 A1 | 11/2008 | Nordahn et al. |
| 2009/0136050 A1 | 5/2009 | Hakansson et al. |
| 2009/0138062 A1 | 5/2009 | Balslev |
| 2009/0192345 A1 | 7/2009 | Westerkull et al. |
| 2009/0288489 A1 | 11/2009 | Lee et al. |
| 2009/0304214 A1 | 12/2009 | Xiang et al. |
| 2010/0041940 A1 | 2/2010 | Hillbratt et al. |
| 2010/0080398 A1 | 4/2010 | Waldmann |
| 2010/0086143 A1 | 4/2010 | Norgaard et al. |
| 2010/0303269 A1 | 12/2010 | Baechler |
| 2010/0310103 A1 | 12/2010 | Baechler et al. |
| 2011/0022119 A1 | 1/2011 | Parker |
| 2011/0026721 A1 | 2/2011 | Parker |
| 2011/0026748 A1 | 2/2011 | Parker |
| 2011/0106508 A1 | 5/2011 | Boretzki |
| 2011/0194706 A1* | 8/2011 | Shim ................. H04R 25/70 381/60 |
| 2011/0301729 A1 | 12/2011 | Heiman et al. |
| 2014/0050341 A1 | 2/2014 | Flynn et al. |

FOREIGN PATENT DOCUMENTS

| | | |
|---|---|---|
| WO | 9806330 A1 | 2/1998 |
| WO | 9907311 A1 | 2/1999 |
| WO | 0193627 A2 | 12/2001 |
| WO | 2005029915 A1 | 3/2005 |
| WO | 2005122887 A2 | 12/2005 |
| WO | 2007102894 A2 | 9/2007 |
| WO | 2007107292 A2 | 9/2007 |
| WO | 2007140367 A2 | 12/2007 |
| WO | 2008049453 A1 | 5/2008 |
| WO | 2009124005 A2 | 10/2009 |
| WO | 2009124008 A1 | 10/2009 |
| WO | 2009124010 A2 | 10/2009 |
| WO | 2010017579 A1 | 2/2010 |

OTHER PUBLICATIONS

Michael Nolan et al., "Transcranial attenuation in bone conduction audiometry", The Journal of Laryngology and Otology, Jun. 1981, vol. 95, pp. 597-608.
Henry et al., "Bone Conduction: Anatomy, Physiology, and Communication," Army Research Laboratory, May 2007.
European Patent Application No. 02 736 403.3, Office Communication dated Oct. 17, 2008.
European Patent Application No. 02 736 403.3, Office Communication dated Apr. 27, 2009.
European Patent Application No. 02 736 403.3, Office Communication dated Apr. 13, 2010.
Extended European Search Report for European Patent Application No. 09727994.7 dated Nov. 12, 2012.
Extended European Search Report for European Patent Application No. 09806222.7 dated Nov. 19, 2012.
International Search Report for PCT/SE2002/001089, dated Oct. 1, 2002.
International Preliminary Report on Patentability for PCT/SE2002/001089, dated Sep. 17, 2003.
International Search Report and Written Opinion for PCT/AU2009/001010, dated Nov. 25, 2009.
International Search Report and Written Opinion for PCT/US2009/038879, dated May 22, 2009.
International Search Report and Written Opinion for PCT/US2009/038884, dated Jun. 22, 2009.
International Search Report and Written Opinion for PCT/US2009/038890, dated May 29, 2009.
International Preliminary Report on Patentability for PCT/US2009/038890, dated Apr. 10, 2010.
Office action and Search Report for Chinese Patent Application No. 201280021764.8 dated Nov. 27, 2015.
International Search Report and Written Opinion for International Application No. PCT/IB2012/051380 dated Nov. 7, 2012.

\* cited by examiner

FITTING OF HEARING DEVICES

CROSS-REFERENCE TO RELATED APPLICATIONS

The present application is a Continuation Application of U.S. patent application Ser. No. 14/006,808, filed Oct. 24, 2013, naming Mark Flynn as an inventor, which is a National Stage of PCT/IB2012/051380, filed Mar. 22, 2012, which claims priority to U.S. Provisional Application No. 61/466,832, filed Mar. 23, 2011. The entire contents of these applications are incorporated herein by reference in their entirety.

BACKGROUND

Field of the Invention

The present invention generally relates generally to hearing devices, and more particularly, to fitting of hearing devices.

Related Art

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, certain types of hearing prostheses commonly referred to as bone conduction devices, convert a received sound into mechanical vibrations. The vibrations are transferred through the skull to the cochlea causing generation of nerve impulses, which result in the perception of the received sound. Bone conduction devices may be a suitable alternative for individuals who cannot derive sufficient benefit from acoustic hearing aids, cochlear implants, etc.

Other types of hearing prostheses commonly referred to as middle-ear implants, also convert received sound into vibrations. The vibrations are delivered to the middle ear or inner ear, and are thereafter transferred to the cochlea causing generation of nerve impulses, which result in the perception of the received sound.

SUMMARY

In a first aspect of the present invention, there is provided a method for fitting a hearing device for a recipient, the method comprising: obtaining threshold levels for the recipient unaided by the hearing device; obtaining threshold levels indicative of a minimum signal for the hearing device that causes a hearing percept by the recipient; calculating a transmission loss using the stored thresholds unaided by the device and the thresholds for the device; generating one or more control settings using the calculated transmission loss; and providing the control settings to the hearing device so that the hearing device applies a gain to sound received by the hearing device that separately compensates for the transmission loss and a hearing loss of the recipient.

In another aspect, there is provided a fitting system for determining control settings for a hearing device, the fitting system comprising: a device comprising: a processor; a storage; and an interface configured to connect to the hearing device; a user interface connected to the device to enable user interaction with the device; wherein the storage of the device stores information indicative of thresholds for a recipient unaided by the hearing device; and wherein the processor is configured to determine threshold levels indicative of a minimum signal for the hearing device that causes a hearing percept by the recipient, calculate a transmission loss using the stored thresholds unaided by the hearing device and the thresholds with the device; generate one or more control settings using the calculated transmission loss, and provide the control settings to the hearing device via the interface so that the hearing device applies a gain to sound received by the hearing device that separately compensates for the transmission loss and a hearing loss of the recipient.

In another aspect of the present invention, there is provided a method for providing a hearing percept using a hearing device, comprising: attaching the hearing device to a recipient; receiving a sound signal by the hearing device; applying a gain to the sound signal to obtain an adjusted signal, wherein the gain separately compensates for a transmission loss and a hearing loss; applying the adjusted signal to the recipient using the hearing device to cause a hearing percept by the recipient.

In another aspect there is provided a hearing device, comprising: a microphone configured to generate a signal based on a received sound signal; a signal processing unit configured to amplify the signal from the microphone, wherein the signal processing unit applies amplification that separately compensates for a transmission loss and a hearing loss of a recipient of the hearing device; an interface configured to allow the hearing device to communicate with an external device; and at least one memory unit for storing control data for controlling the signal processing unit; wherein the interface is adapted to receive control settings from the external device for providing stimulation to the recipient to cause a hearing percept in the user based on the received sound signal.

BRIEF DESCRIPTION OF THE DRAWINGS

Embodiments of the present invention are described herein with reference to the accompanying drawings, in which.

DETAILED DESCRIPTION

Aspects of the present invention are generally directed to fitting a hearing device for a recipient in which the device transmission losses and the recipient hearing losses are separately compensated for, thereby improving the accuracy of the fitting data.

Specifically, the fitting process includes in-situ measurements of the recipient with the hearing device. An embodiment uses these in-situ measurements to calculate transmission losses in the path sound travels from the hearing device to the recipient. In an embodiment, the transmission losses are calculated by subtracting threshold measurements obtained without the hearing device from in-situ threshold measurements. In use, the hearing device applies gain that separately compensates for the transmission and hearing losses.

The following description of an embodiment will be discussed with reference to one type of hearing device, a bone conduction device. It should be understood that embodiments of the present invention may be implemented in other types of hearing devices, such as, for example, middle or inner ear mechanical stimulation systems (e.g., DACS) and hearing aids.

Figure 1:
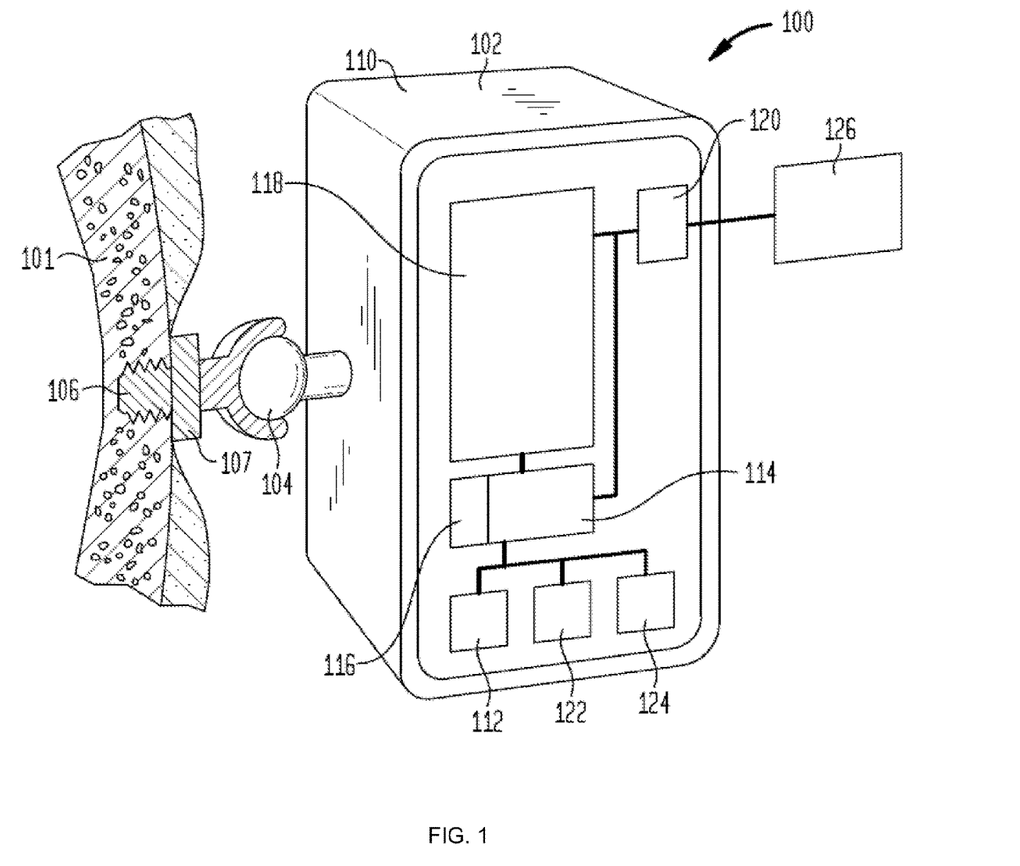
FIG. 1 is a schematic overview of a bone-anchored hearing device in accordance with an embodiment of the present invention.

FIG. 1 illustrates a bone-anchored hearing device ("hearing device") 100 that transmits sound information to a recipient's inner ear via the skull bone 101. The hearing device includes a detachable body portion 102, a coupling arrangement or portion ("coupling arrangement") 104 and an implantable fixture or anchor ("fixture") 106. The fixture is preferably implanted and osseointegrated in the bone behind the external ear. The detachable body portion may then be coupled to the fixture using coupling arrangement 104, allowing sound to be transmitted via the skull bone to the cochlea (inner ear).

In one embodiment, fixture 106 is anchored into the mastoid bone behind the outer ear; however, the fixture may be implanted under skin within muscle and/or fat or in any other suitable manner. The hearing device 100 may be anchored in any suitable manner or position. Fixture 106 is preferably made of titanium, since titanium may be integrated into the surrounding bone tissue (i.e., osseointegration); however, the fixture may be any suitable material or combination of materials.

Preferably, as stated above, the detachable body portion 102 is connected to fixture 106 via coupling arrangement 104. In some embodiments, coupling arrangement 104 may be a bayonet coupling or mechanical spring coupling; however the coupling arrangement may be any suitable coupling. The hearing device may include, in addition to the titanium fixture, a spacer element or skin penetrating member 107 which may be connected to the bone anchored titanium fixture by a spacer screw or in any other suitable manner.

In one embodiment, the detachable portion includes housing 110, which is preferably formed from plastic, but may be formed from any suitable material and be any suitable shape or size. The detachable portion 102 preferably includes a microphone 112 (or other suitable sound input device), an electronic unit 114, a battery 116, a vibrator 118, a first memory unit 122, a second memory unit 124 and a data interface 120. It is noted that the hearing device 100 does not need to include each of these elements and may include all, some or none and may include any additional desired elements.

In one embodiment, microphone 112 acquires sound and generates a signal which is sent to the electronic unit 114. Preferably, electronic unit 114 is battery powered and may be a signal processing unit that amplifies the signal from the microphone 112. In one embodiment, the electronic unit 114 is equipped with an electronic filtering device arranged to reduce the amplification in the signal processing chain of the hearing device; however, the electronic unit 114 may be equipped with any suitable components and does not necessarily include a filtering unit. The amplified signal is supplied to a vibrator 118 that converts the electrical signal into vibrations which are then transferred to the skull bone via the titanium fixture 106.

In one embodiment, the hearing device 100 includes at least one memory unit, in communication with, connected to or integrated within the electronic unit 114. Preferably, the memory unit includes a first memory unit 122 for short-term storage, such as a RAM-memory device, and a second memory unit 124 for long-term storage, such as an EEPROM, flash or other suitable non-volatile memory device; however, it is noted that the hearing device may include any number and/or type of memory units. The memory units are configured to store control data for controlling the signal processing in the electronic unit 114.

In one embodiment, the hearing device includes a data interface 120 that enables data communication between the hearing device (e.g., the electronic unit 114) and an external control device or system ("external device") 126. As stated above, the external device may be external device such as a fitting system, PDA, computer, mobile phone, or any other suitable device. Preferably, the interface allows two-way or bidirectional communication. That is, interface data may be sent from both the electronic unit 114 and the external device 126. For example, in one embodiment, the interface may be adapted to receive control signals from the external device for generating vibrations in the vibrator at predetermined frequencies, and receive control settings for the electronic unit for storing in the memory unit. In some embodiments, however, the interface is a one way interface, allowing only data to be forwarded from the external device 126 to the hearing device. In other embodiments, communication is a one way interface with data being forwarded from the hearing device to any type of receiving device. The data may include measured control signals or any type of status information or other suitable data. This information may be used to merely monitor the hearing device or be used with a control device that may be a separate device or be integrated into the hearing device or be any other suitable device.

Figure 2:
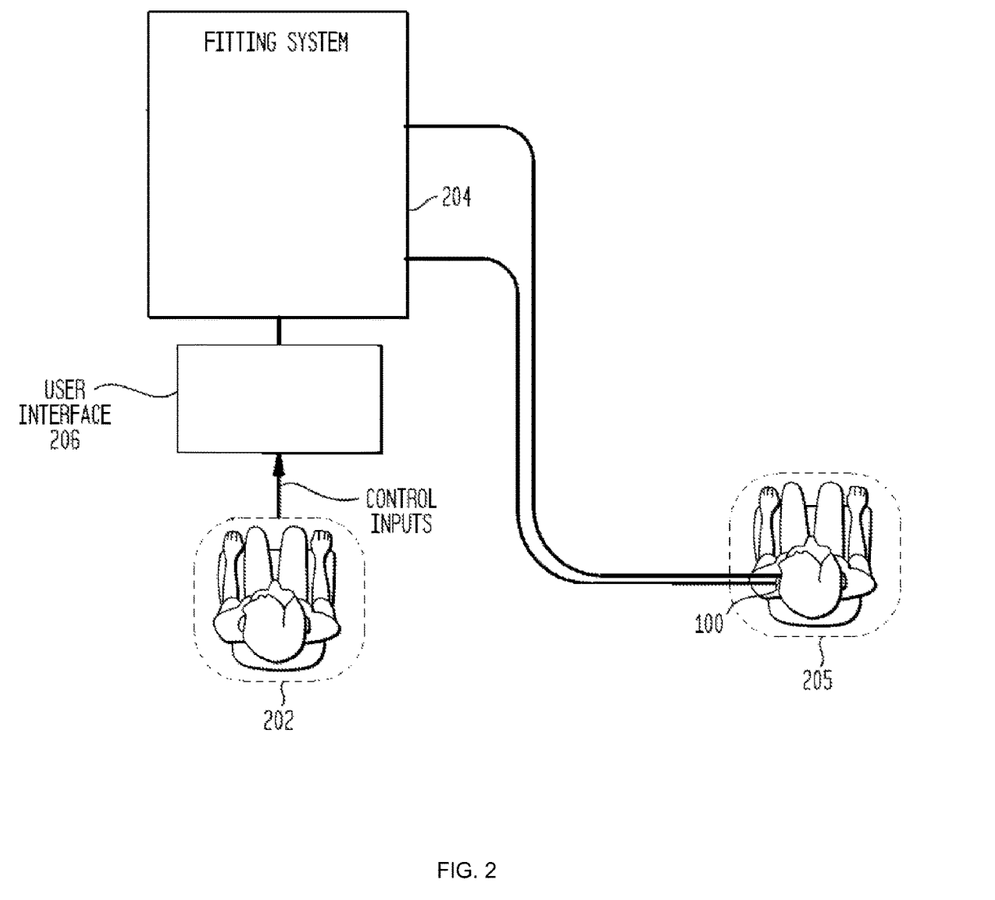
FIG. 2 is a schematic diagram of an exemplary external device in which control settings for a bone conduction hearing device are generated and stored in the hearing device.

FIG. 2 is a schematic diagram in which hearing device 100 (FIG. 1) has its control settings altered by a third party 202 (referred to hereinafter as audiologist 202) using an exemplary external control system or device ("external device") 204. Specifically, FIG. 2 illustrates a fitting system in which an audiologist sets or alters the control settings. It is noted however, that, as stated herein, the external device does not necessarily need to be a fitting system and may be any suitable external device and does not need to be operated by an audiologist, but may be operated by any suitable third party or the recipient 205. As described below, external device 204 permits a audiologist 202 to configure hearing device 100 (FIG. 1) for a recipient.

As shown in FIG. 2, audiologist 202 uses an external device 204 that includes interactive software and computer hardware to configure individualized recipient control settings that are used for subsequent hearing device operations by electronic unit 114 (FIG. 1). External device 204 may interact with the audiologist 202 via a user interface 206 configured to present information to the audiologist and receive information from the audiologist. For example, user interface 206 may include a display (e.g., LCD, touch screen, etc.), keyboard, mouse, etc. Further, although illustrated separately, external device 204 and user interface 206 may be a singular device (e.g., PDA, laptop computer, etc.) Although FIG. 2 illustrates only a single hearing device 100, it should be understood that in embodiments, external device 100 may also be used to fit binaural systems in which a hearing device 100 is fitted to each ear of recipient 205.

External device 204, in the present embodiment, is configured to measure the threshold for the device, such as the minimum level (e.g., in terms of millivolts) that causes a hearing percept by the recipient. Traditionally, thresholds for the device were measured and treated as indicative of the total hearing loss of the individual. Amplification by the hearing device 100 was thus applied as if these measured thresholds were the actual hearing thresholds.

Treatment of Sensorineural Hearing Loss (SNHL) typically requires that the amplification gain be equal to a fraction of the hearing loss (e.g., 33-55% of the measured hearing loss). However, any loss through the transmission should be fully compensated (i.e., 100%). By determining the amplification based on the measured thresholds being treated as actual thresholds, the transmission losses may not be appropriately handled. This can result in under amplification by the hearing device.

In an embodiment, external device determines the transmission losses that effect sound provided by the hearing device. These transmission losses may include, for example, losses due to the coupling of the hearing device to the recipient. Depending on the type of hearing loss and connection type, these transmission losses may further include transcranial attenuation, attenuation due to the patient's skin, skull attenuation etc. For example, for recipient's suffering from SSD and with an abutment connection, the transmission losses may include skull attenuation, transcranial attenuation but not skin attenuations. External device then generates control settings that are provided to the hearing device so that the hearing device, in use, fully compensates for the measured transmission losses and applies a gain he is a fraction of the hearing loss (e.g., 33-55%).

As will be discussed further below, in an embodiment, external device 204 further enable audiologist 202 to measure, for a plurality of frequency channels, the lowest level (i.e., a threshold level) in terms of decibels of Sound Pressure Level (dB SPL) that evokes a hearing percept in the recipient 205 in the absence of using the hearing device. This measured level determined without the device is indicative of the total hearing loss of the recipient That is, the difference between the measured threshold without the device and the threshold of person with normal hearing is the hearing loss of the recipient.

Although in the presently discussed embodiment, the audiogram for the recipient in terms of dB SPL is determined using external device 204, it should be understood that in other embodiments a separate system may be used for taking these measurements than is used for other steps of the presently discussed method. Further, the thresholds without the device may be determined and stored by the external device prior to attaching the hearing device to the recipient.

As noted, in an embodiment the fitting system calculates the transmission loss experienced. In calculating this transmission loss, in an embodiment, external device 204 subtracts the thresholds measured using the hearing device from the thresholds measured in the absence of the device.

Further, in an embodiment, external device is provided with certain information useful in calculating the transmission losses and/or the best method to be used for compensating for a given hearing and transmission loss. For example, in an embodiment in which the hearing device is a bone conduction hearing device, external device 204 asks the audiologist 202 (e.g., audiologist) to specify the type of hearing loss (e.g., conductive, mixed, or single sided deafness (SSD)) and also the type of connection (e.g., abutment, softband/headband, demo (e.g., a temporary abutment attached to the recipient using, for example, an adhesive) used by the hearing device. Each of these factors affects the transmission of sound from the bone anchored hearing device to the cochlea and is thus useful in calculating the transmission loss. As will be discussed further below, this provided information may be used by external device 204 in generating the control settings provided to the hearing device by the external device. Other types of information may be provided for other types of devices. For example, for a hearing aid, the information may include the type of tubing and/or venting used by the device. Further, these selections (e.g., connection type) may also be used in the fitting process, for example, to determine the amount of available gain for the hearing device as well a the feedback limits for the hearing device.

Figure 3:
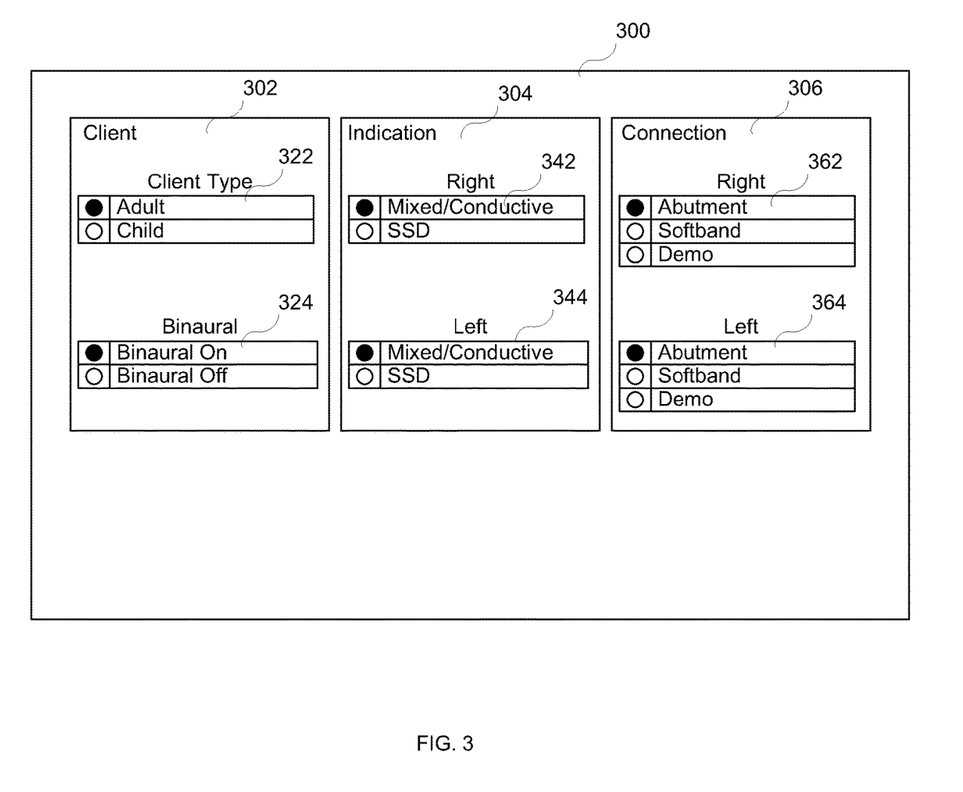
FIG. 3 illustrates an exemplary graphical user interface (GUI) that may be presented to a third party to permit the third party to specify the type of hearing loss and type of connection, in accordance with an embodiment of the present invention.

FIG. 3 illustrates an exemplary graphical user interface (GUI) that may be presented to an audiologist to permit the audiologist to specify the type of hearing loss and type of connection, in accordance with an embodiment of the present invention. As illustrated, GUI 300 includes a section for entering client information 302 regarding the recipient, indication information 304 regarding the type of hearing loss, and connection information 306 regarding the type of connection used by the hearing device. As shown, the client information 302 allows the audiologist of specify the client type 322 (e.g., adult or child) and whether or not the recipient's system is a binaural system or not 324. As shown, the audiologist may select the client type 322 and whether the system is binaural 324 by selecting buttons next to the appropriate selection. GUI 300 may be displayed by external device 204 using user interface 206. Selection of binaural may be used by the fitting system to apply a binaural compensation to the control settings to, for example, increase or decrease the gain to compensate for bilateral summation.

As shown, the indication information 304 allows the audiologist to specify the type of hearing loss experienced by the recipient. This information 304 may be individually specified for both the right ear 342 and left ear 344 of the recipient. As shown, in this example, the audiologist may select (by selecting the appropriate button) for each ear whether the hearing loss is mixed/conductive or SSD. As shown, the connection information 306 allows the audiologist to individually specify for the right ear 362 and left ear 364 by selecting the appropriate button whether the connection type is abutment, softband, or demo. It should be understood that this example is only exemplary and that in other embodiments other types of selections may be used (e.g., additional connection types may be selected). Specifying the hearing loss type and the connection creates a structure through which the best estimation of hearing loss and transmission loss is calculated in an embodiment.

Figure 4:
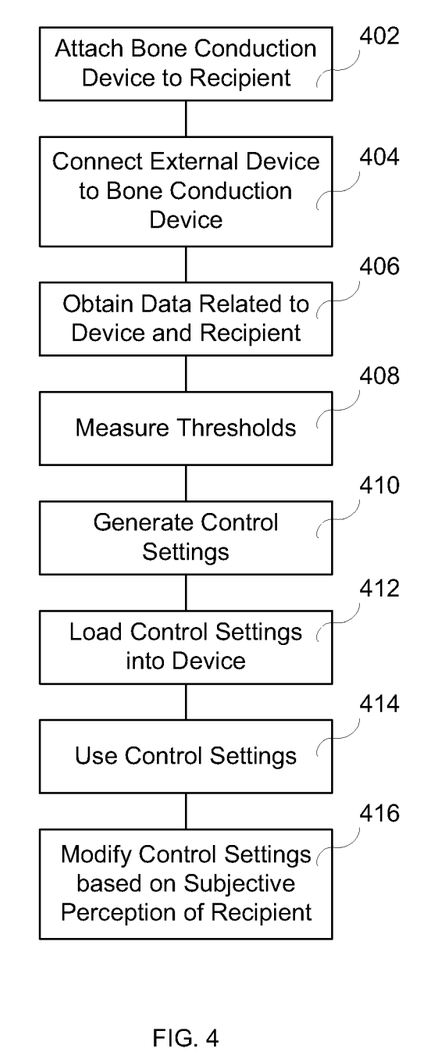
FIG. 4 is a high-level flow chart for fitting a hearing device using an external device, in accordance with an embodiment of the present invention.

FIG. 4 is a high-level flow chart illustrating a method of determining the control settings of a hearing device according to one embodiment of the present invention. FIG. 4 will be discussed with reference to the above-discussed FIG. 2 and the hearing device will be assumed to be a bone conduction hearing device. It should, however, be understood that in other embodiments, the hearing device may be other types of hearing devices, such as middle or inner ear mechanical stimulation devices (e.g., Direct Acoustic Cochlear Stimulation (DACS) systems), hearing aids, etc. For simplicity, in the below description, only a single hearing device is fitted to the recipient. It should, however, be understood that the method may also be used with binaural systems.

In the illustrative embodiments, at block 402 the hearing device 100 is attached to the recipient 205. At block 404, the external device 204 is connected to the hearing device 100. The external device 204 may be coupled to the hearing device 100 using wires, wirelessly or in any other suitable manner. At block 406, information is obtained regarding the hearing device 100 and the recipient 205. This information is obtained, for example, using a GUI such as discussed above with reference to FIG. 3. In the presently discussed embodiment, the information obtained by external device 204 includes, for example, information regarding the recipient (e.g., adult/child, binaural or mononaural system), information regarding the type of hearing loss experienced by the recipient (e.g., Conductive, Mixed, SSD), and information regarding the connection type (e.g., abutment, softband, demo). Although this information is obtained using a GUI in this example, this information may be obtained in other embodiments using different techniques. For example, in an embodiment, hearing device 100 may store or otherwise determine one or more of these parameters (e.g., connection type) and provide this information to external device 204. Or, for example, information such as this information may be input to the external device separately from the fitting software, such as, for example, by programming using buttons, etc.

At block 408, external device 204 measure the thresholds for the recipient. As noted above, in this example, external device 204 obtains thresholds (the lowest level at which the recipient can perceive sound) in terms of dB SPL. These threshold are obtained for a number of frequencies across the normal hearing frequency range (e.g., 20-20 kHz). Any suitable technique may be used for obtaining the thresholds. Further, these thresholds may be obtained, for example, without the hearing device attached to the recipient. This obtained data may be in the form of an audiogram and include both threshold and maximum comfort level data. This data will be referred to herein as Bone Conduction Audiogram (BCA) data when the hearing device 100 is a bone conduction device. Further, although, in the present embodiment external device 204 is used to measure the BCA data, in other embodiments, this data may be measured using a separate device(s) and the external device 204 used for performing the other steps of FIG. 4. For example, the BCA data may be obtained by a separate audiologist and stored by the external device 204 prior to commencement of the method of FIG. 4. Methods for measuring a BCA (e.g., a "Normalized BCA" also knows a threshold based on Sensorineual Hearing Loss (SNHL) without attenuations) for a recipient are well known to those of skill in the art, and, as such, are not discussed further herein. The used BCA is preferably loss free.

In addition to obtaining audiogram data, the hearing device 100 also measures the thresholds by applying stimulation to the recipient using the hearing device and determining the minimum signal (e.g., in terms of mV) that causes a hearing percept by the recipient. For example, in one embodiment, a stimulus with a predetermined voltage (in terms of mV) is generated using the external device 204 and provided to the hearing device 100. This signal vibrates the vibrator of the hearing device 100 to cause a sound percept in the recipient. Although in this embodiment, the vibrator in the hearing device is used to generate vibrations, in other embodiments an external sound source or vibration source (not shown), controlled by the external device 204, may be used for generation the vibrations. If an external vibration source is used, it is preferably coupled to the fixture 106 (FIG. 1). By coupling the external vibration source to the fixture 106, more accurate measurements may be generated for the recipient's bone conduction thresholds. Once the bone conduction thresholds are measured using the external vibration source, they are converted to the hearing device. Such conversion could be accomplished by using accelerometers to determine the relative compensation. That is, as one of ordinary skill in the art would understand, the vibration of the hearing device and the external vibration source could be measured using accelerometers at the same voltage and the difference is the compensation value. However, it is noted that, if desired, any external vibration source may be used. For example, a vibration device that is pressed against the skin or held between the teeth may be used.

Using the vibrator in the hearing device may provide more accurate measurement data. For example, using the vibrator in the hearing device would allow measurement of the influence of the specific sound conduction conditions, such as resonance levels occurring in the hearing device, in the connection between the hearing device and the skull bone, or in the patients head. Further, as stated above, measurements based on the hearing device itself may eliminate the risk of conversion errors and the like (e.g., the compensation value using accelerometers).

In one embodiment, the recipient or audiologist may repeatedly send signals to the hearing device at a specific frequency until a hearing percept is provided to the recipient. During this procedure, the recipient indicates if a sound is perceived at a specific frequency. Such indication may be verbal, non-verbal or any desired indication. If the recipient does not perceive a sound, no indication is provided. If no indication is provided, the mV output is increased by a desired or predetermined level using the external device. This increase in mV output is continued until the recipient indicates that the sound is perceived or until a suitable level of sound percept is achieved. The lowest level at which an indication is received from the recipient is the threshold level in terms of mV.

Once the recipient indicates that sound is perceived, the audiologist may indicate such via the user interface 206 and the threshold level in terms of mV automatically stored for the frequency being tested. In another embodiment, the audiologist or the recipient may have the choice of storing that control setting when the recipient indicates that the threshold has been met or not storing the control setting and storing a different value for percept at sound for that frequency. This data obtained using hearing device 100 applying stimulation will be referred to herein as BCDirect or BCD data when the hearing device 100 is a bone conduction device.

The threshold measured at block 408, as noted, may be obtained at plurality of frequencies over the hearing frequency range. Although both the BCA data and BCDirect data are obtained at block 408 in the present embodiment, it should be understood that this data may be obtained at different steps. For example, the BCA data may be obtained prior to attachment of the hearing device to the recipient, and only the BCDirect data obtained at block 410.

Figure 6:
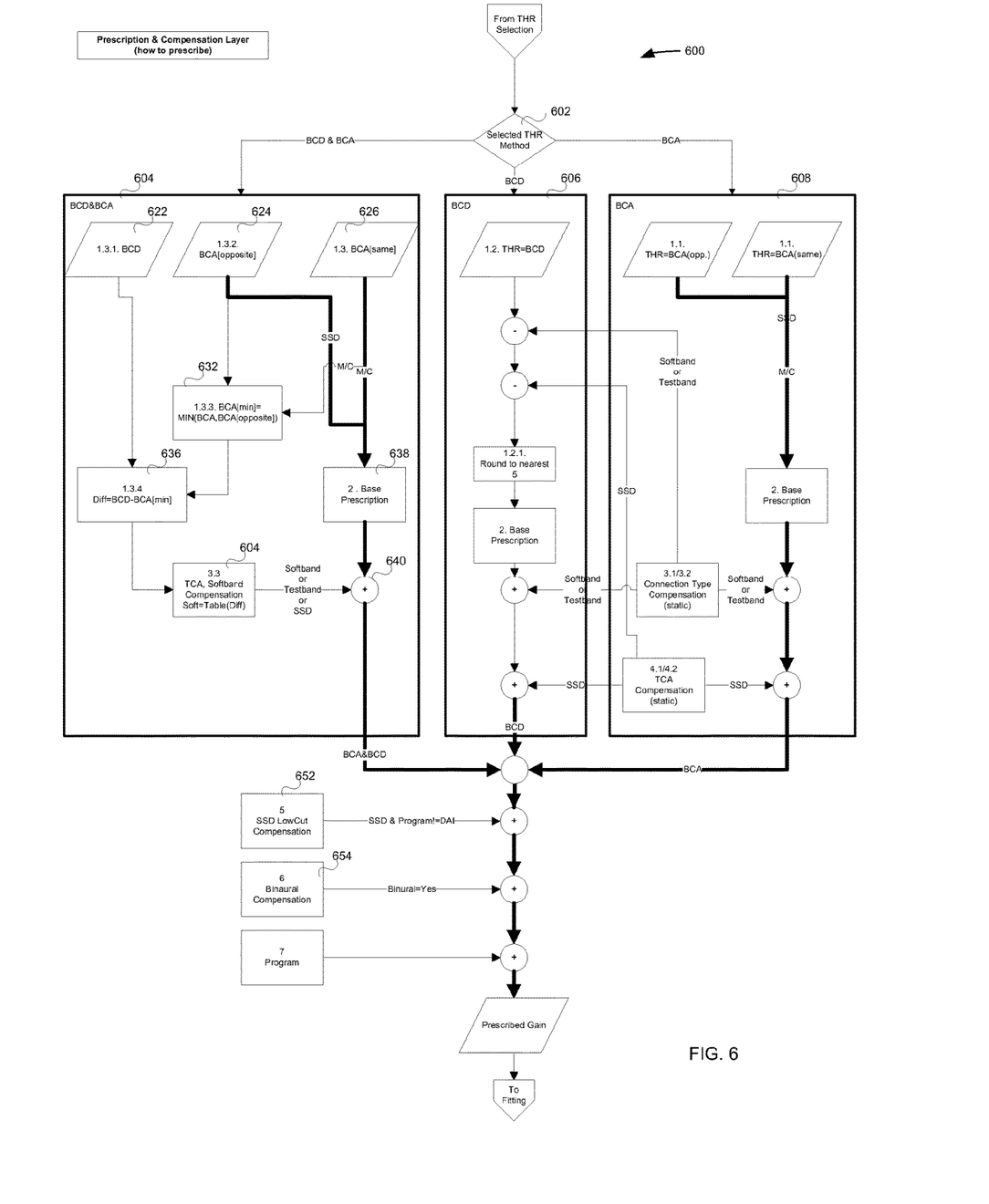
FIG. 6 provides a more detailed flow chart of method external device 204 may use for generating control settings, in accordance with an embodiment of the invention.

Although the above discussion provided an example for obtaining BCDirect data for an individual hearing device, in an embodiment a similar mechanism may be used to obtain information that may be used to determine a binaural compensation value for binaural systems. For example, in an embodiment a common tone may be provided by both hearing devices of a binaural system. The amplitude of this tone may be increased until it is perceived by the recipient to determine a threshold level for the binaural system. The difference between the binaural threshold and the unilateral threshold (e.g., for a singular hearing device) provides a benefit of the binarual system. This difference can thus be used to generate a compensation value for the binaural system that may be used to adjust the gain of the system, such as will be discussed further below with reference to block 654 of FIG. 6. For example, if the difference indicates that the binarual system provides a determined benefit, this benefit may be used to reduce the determined gain at block 654 (FIG. 6). This binaural compensation value may be based on, for example, a percentage (e.g., 100%, 75%, 50%, etc.) of the calculated benefit.

The external device 204 generates the control settings (e.g., gains) for the hearing device 100 at block 410. As noted above, in an embodiment, external device 204 calculates the transmission loss in determining the control settings. For example, in the presently discussed embodiment, the external device 204 uses the audiogram data (e.g., BCA) and the device data (e.g., BCDirect) to calculate the transmission loss. The external device then determines control settings so that the hearing device 204 may apply gain for the transmission loss and hearing loss separately. For example, as noted above, transmission loss is compensated for in a 1:1 fashion (i.e., the gain applied to make up for transmission loss is set to make the signal equal to what the signal would have been had there been no transmission loss). The hearing device 100 calculates the gain for the hearing loss at a value equal to a fraction of the hearing loss (e.g., 33-50%) of the measured hearing loss. In an embodiment, gain is calculated using the formula: Gain=transmission loss (1:1)+(1/x*threshold), where transmission loss is the gain calculated to 100% compensate for transmission losses and 1/x is the fraction used for calculating the gain used to compensate for hearing losses.

Applying the gain separately for the transmission loss and hearing loss may provide a more accurate fitting. For example, in an embodiment, recipient 205 is fitted with a bone conduction device attached via a headband/softband. The audiogram is determined for the recipient and then the BCDirect data is calculated. The hearing device 100 (in this case a bone conduction device) applies gain separately for the hearing loss and the transmission loss components. This example becomes more complex for other implementations, such as when the patient suffers from SSD and is fitted with a bone conduction device attached via a softband where the effect of the softband and transcranial attenuation are accounted for.

At block 412, the external device 204 loads the calculated control settings (e.g., gains or data useable for calculating the gains) into the hearing device 100. The hearing device 100 then uses the loaded control setting 100 at block 414. At block 416, the control settings may be adjusted based on the subjective perception of the user. For example, based on the subjective perception of the recipient, it may be determined that the recipient prefers different settings for different acoustic environments, such as listening to music, driving, watching television, etc. Audiologist 202 makes such subjective adjustments to the control setting using external device 204 at block 416. That is, block 416 enables audiologist 202 to make minor adjustments to the settings based on the subjective experience of the recipient.

Figure 5:
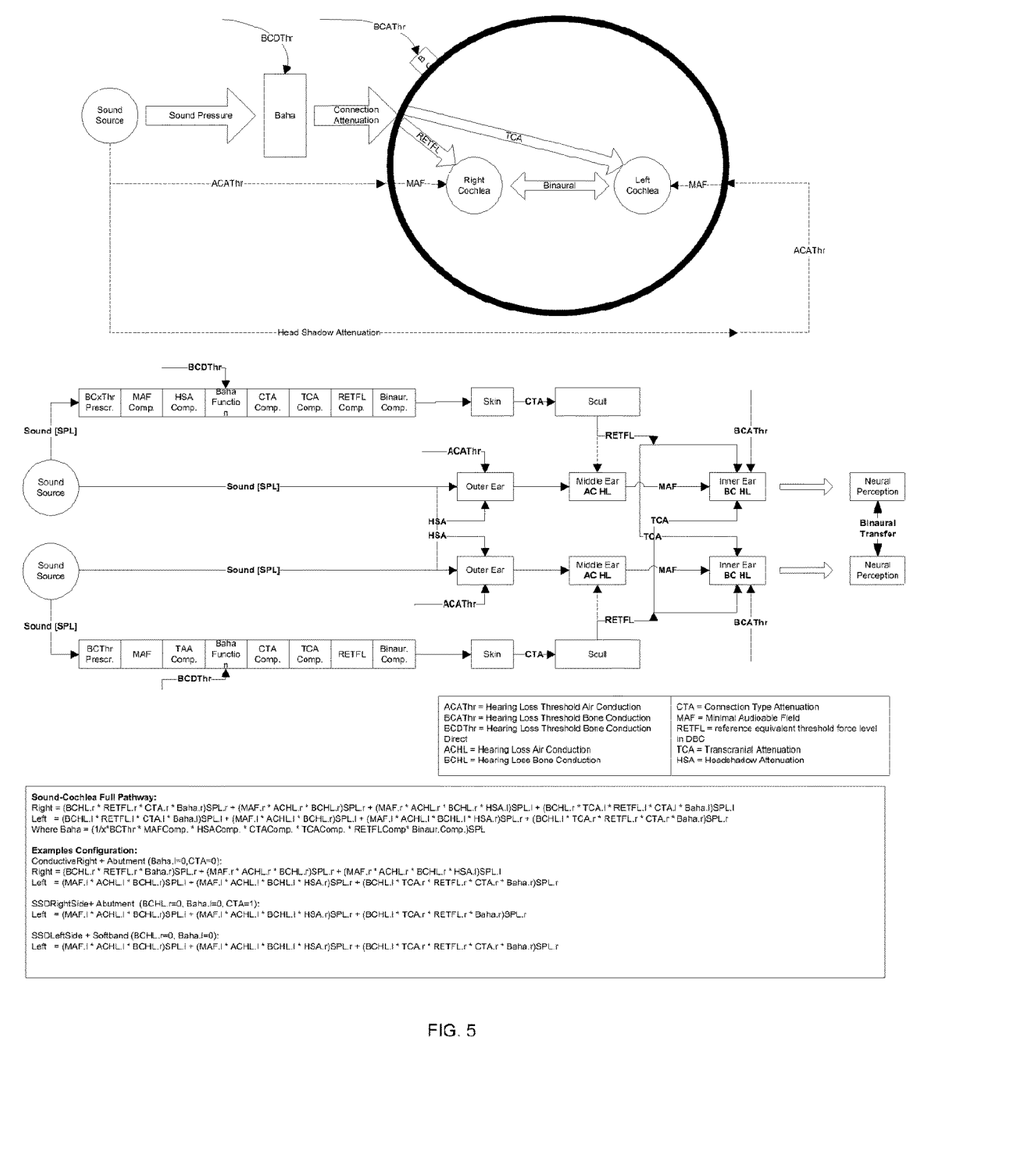
FIG. 5 provides an exemplary diagram to illustrate transmission losses they may occur in the path of sound provided to a recipient of a hearing device and BAHA gain compensations that may be invoked based upon the patient indications.

FIG. 5 provides an exemplary diagram to illustrate transmission losses that may occur in the path of sound provided to a recipient of a hearing device and BAHA gain compensations that may be invoked based upon the patient indications. Using the illustrated formulas and the information provided at block 406, external device 204 may calculate the actual transmission loss along the sound path for the recipient.

FIG. 6 provides a more detailed flow chart of method external device 204 may use for generating control settings, in accordance with an embodiment of the invention. The flow chart 600 illustrates that at decision 602 one of three methods for calculating the control settings (e.g., gain) is selected. This selection may be made, for example, by external device 204 automatically based on the presence of data input to the external device, such as the data input at block 406 and the type of BCA and/or BCDirect data available. Or, for example, the decision may be made by audiologist 202 using user interface 206.

The middle flow 606 (labeled BCD) is selected when only BCD is present and assumes there may be transmission loss already included in the BCD threshold. Whatever is measured through hearing device (e.g., using its sound processor) is assumed to be the hearing and transmission loss. Thus, the transmission loss must be subtracted from the thresholds prior to get a normalized threshold. Then the gain rule is applied and the transmission compensations are added. If there are no loss indication(s) made in 304, 306, the subtractions/compensations are redundant and not applied. An example, where this flow may be selected is for a person with a conductive/mixed hearing loss measured with BCD only and the connection type is an softband, then softband loss is subtracted, hearing loss gain applied and then softband compensations added.

The far right flow 608 (labeled BCA) is selected for situations where the only known information is from the recipient's audiogram. Here the gain is calculated based on the hearing loss, with additional gain added for the average transmission factor. As the actual transmission loss is unknown, published (or collected) normative values are used for the transmission loss. Flow 608 may be selected, for example, where the recipient suffers from SSD hearing loss, where the transcranial attenuation value is added to the required gain or when the recipient is listening through a softband where these transmission loss values are added to calculated required gain.

The far left flow 604 (labeled BCD&BCA) is used when the external device 204 knows the audiogram (BCA data) and BCDirect values. Further, in an embodiment, flow 604 is only selected if the indication is SSD or the connection type is either softband/headband or demo. Otherwise flow 606 or 608 (depending on whether BCA or BCDirect data is available and the most recent) is selected if the connection type is abutment. It should be noted, however, that this is but one set of exemplary conditions that may be used for selecting flow 604 and in other embodiments other selection criteria may be used. For example, in an embodiment, only flow 604 may be included and is thus always used by the fitting system.

External device 204 calculates the transmission loss using the BCDirect and BCA data in flow 604. This transmission loss then has the gain separately applied from the gain applied for the hearing loss, as discussed above. The BCS&BCA flow 604 may be selected, for example, when the patient with a headband/softband connection type and the audiogram is known and the BCD is calculated.

A further description of the BCD&BCA flow 604 will now be provided. At the start of the flow 604, BCDirect data 622, BCA (opposite) data 624, and BCA (same) data may be available. BCDirect data 622 is the threshold data obtained using the hearing device. BCA (opposite) data 624 is the audiogram data (without the device) for the ear opposite the ear for which the hearing device is providing stimulation. BCA (same) data 626 is audiogram data for the ear on the same side as the hearing device. For SSD patients, BCA (same) data 626 may not be available due to, for example, the recipient being deaf in that ear.

External device 204 determines the best case hearing loss for the recipient at block 634. As shown, external device 204 compares the BCA (opposite) data 624 and BCA (same) data 626 to determine the minimum hearing loss for the recipient. This determination may be made on a frequency channel basis, such that a different minimum is determined for each frequency channel of the hearing device.

External device 204 subtracts the minimum hearing loss determined at block 634 from the BCDirect data 622 to obtain a difference: Diff=BCD−min[BCA]. This difference corresponds to the transmission loss along the path of sound provided from the hearing device to the recipient. External device 204 then consults a stored table to determine the compensation to be applied to account for the transmission loss at block 636. In an embodiment, the transmission losses are 100% compensated. In such, an embodiment, block 636 may not be used and instead the compensation to be applied is simply the difference computed at block 634. In other embodiments, the stored table may specify different compensations for different characteristics of the recipient (e.g., adult/child, binaural/monoaural, etc.) and/or characteristics of the hearing device (e.g., softband/demo connection type, etc.)

External device 204 generates a base prescription for providing stimulation to the recipient at block 638. This base prescription includes a gain to be applied that is based on the hearing loss of the recipient. External device 204 may determine this gain by looking up the hearing loss for the recipient in a stored table that specifies the gain to be used for a given hearing loss. As shown, external device 204 uses the BCA (same) data 626 to determine the gain for patient's suffering from conductive or mixed hearing losses. External device 204 uses the BCA (opposite) data 624 to determine the gain for patient's suffering from SSD.

External device adds the compensation determined at block 636 (or 634 if a table is not used) to the base prescription at block 640 to obtain a gain for use by hearing device. As noted, this gain may be determined on a frequency channel basis, such that external device 204 determines a different gain for each frequency channel of the hearing device. Further, this determined gain separately compensates for the hearing loss of the recipient and the transmission loss of sound provided from the hearing device to the recipient.

As shown, external device 204 may also add additional compensation values to this determined gain. For example, for SSD recipient's external device may add a SSD lowcut compensation 652 that compensates for the head shadow effect. External device 204 may also apply a separate binaural compensation 654 for recipient's fitted with binaural systems. For example, if the recipient is fitted with a binaural system, external device 204 may apply a compensation that reduces the amount of gain to account for binaural summation (i.e., the summation of sound provided by the two bilateral hearing devices of the binaural system). Other additional compensations may be applied based on the specifics of the implementation. These compensations are separate from the compensation for transmission losses determined at block 636

Various techniques for determining the transmission loss from the BCA and BCDirect data. For example, the difference between the BCA and BCDirect values may be calculated. The compensation for the hearing loss may then be obtained by consulting a table stored by external device 204 that specifies compensation values based on calculated difference values.

BCD&BCA flow 604 may provide different types of compensation, such as connection type compensation (based on the type of connection used to connect the hearing device to the skull), Transcranial Attenuation (TCA) compensation for SSD Patients, SSD Lowcut compensation for SSD patients, Binaural compensation (for either one or two hearing aids). The compensation obtained from the lookup tables may be adjusted for either soft or loud gain for each audiological band.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for fitting a hearing device for a recipient, the method comprising:
   obtaining threshold levels for the recipient unaided by the hearing device;
   obtaining threshold levels indicative of a minimum signal for the hearing device that causes a hearing percept by the recipient;
   calculating a transmission loss using the threshold for the recipient unaided by the device and the threshold for the hearing device that causes a hearing percept by the recipient;
   generating one or more control settings using the calculated transmission loss; and
   providing the control settings to the hearing device so that the hearing device applies a gain to sound received by the hearing device that separately compensates for the transmission loss and a hearing loss of the recipient, wherein the transmission loss is at least in part a result of losses at a coupling between the hearing device and the recipient, which coupling has at least a portion that is implanted in the recipient.

2. The method of claim 1, wherein calculating the transmission loss comprises:
   subtracting a threshold unaided by the device from a threshold for the device.

3. The method of claim 1, wherein the hearing device is a bone conduction hearing device.

4. The method of claim 1, wherein the hearing device is a middle ear mechanical stimulation system.

5. The method of claim 1, wherein the hearing device is an inner ear mechanical stimulation system.

6. The method of claim 1, wherein the hearing device is a hearing aid.

7. A fitting system for determining control settings for a hearing device, the fitting system comprising:
   a device comprising:
      a processor;
      a data storage device; and
      an interface configured to connect to the hearing device;
   a user interface connected to the device to enable user interaction with the device;
   wherein the data storage device has stored therein thresholds for a recipient unaided by the hearing device; and
   wherein the processor is configured to:
      determine thresholds indicative of a minimum signal for the hearing device that causes a hearing percept by the recipient, and to calculate a transmission loss using the stored thresholds unaided by the hearing device and the thresholds with the device;
      to generate one or more control settings using the calculated transmission loss; and
      to provide the control settings to the hearing device via the interface so that the hearing device applies a gain to sound received by the hearing device that separately compensates for the transmission loss and a hearing loss of the recipient,
   wherein the transmission loss includes a transmission loss that is at least in part a result of losses at a coupling between the hearing device and the recipient, which coupling has at least a portion that is implanted in the recipient.

8. The fitting system of claim 7, wherein the processor in calculating the transmission loss for a frequency is configured to subtract a threshold unaided by the hearing device from a threshold for the hearing device.

9. The fitting system of claim 7, wherein the hearing device is a bone conduction hearing device, and wherein the system is configured to query a user thereof a type of hearing loss and/or a specific feature of a type of hearing loss and/or is also configured to enable the user to input the type of hearing loss and/or the specific feature of the type of hearing loss.

10. A method for providing a hearing percept using a hearing device, comprising:
   attaching the hearing device to a recipient;
   receiving a sound signal by the hearing device;
   applying a gain to the sound signal to obtain an adjusted signal, wherein the gain separately compensates for a transmission loss and a hearing loss; and
   applying the adjusted signal to the recipient using the hearing device to cause a hearing percept by the recipient,
   wherein the transmission loss is at least in part a result of losses at a coupling between the hearing device and the recipient, which coupling has at least a portion that is implanted in the recipient.

11. The method of claim 10, wherein the applied gain is different for different frequencies of the sound signal.

12. The method of claim 10, further comprising:
   obtaining threshold levels for the recipient in terms of dB SPL indicative of threshold levels of the recipient without the hearing device.

13. The method of claim 12, further comprising:
   obtaining threshold levels, for a plurality of frequencies, indicative of a minimum signal for the hearing device that causes a hearing percept by the recipient at the frequency.

14. The method of claim 13, further comprising:
   calculating the transmission loss using the obtained thresholds without the hearing device and the obtained thresholds for the hearing device.

15. The method of claim 10, herein the hearing device is a bone conduction hearing device.

16. The method of claim 10, wherein the hearing device is a middle ear mechanical stimulation system.

17. The method of claim 10, wherein the hearing device is an inner ear mechanical stimulation system.

18. A hearing prosthesis device; comprising:
   a microphone configured to generate a signal based on a received sound signal;
   a signal processing system configured to amplify the signal from the microphone, wherein the signal processing system applies amplification that compensates for a transmission loss and a hearing loss of a recipient of the hearing device; and
   wherein the hearing prosthesis device is adapted to receive control settings for providing stimulation to the recipient to cause a hearing percept in the user based on the received sound signal such that the hearing percept is based on amplification of the signal from the microphone that compensates for the transmission loss and the hearing loss of a recipient of the hearing device,
   wherein the transmission loss includes a transmission loss that is at least in part a result of losses at a coupling between the hearing device and the recipient, which coupling has at least a portion that is implanted in the recipient.

19. The hearing device of claim 18, wherein the signal processing system applies amplification that separately compensates for the transmission loss and a hearing loss of a recipient of the hearing device, wherein the hearing prosthesis device is adapted to receive control settings for providing stimulation to the recipient to cause the hearing percept in the user based on the received sound signal such that the hearing percept is based on amplification of the signal from the microphone that separately compensates for the transmission loss and the hearing loss of the recipient of the hearing device, and wherein the signal processing-system is configured to apply different gains for different frequencies of the sound signal.

20. The hearing device of claim 18, wherein the signal processing system applies amplification that separately compensates for the transmission loss and a hearing loss of a recipient of the hearing device, wherein the hearing prosthesis device is adapted to receive control settings for providing stimulation to the recipient to cause the hearing percept in the user based on the received sound signal such that the hearing percept is based on amplification of the signal from the microphone that separately compensates for the transmission loss and the hearing loss of the recipient of the hearing device, and wherein the hearing device is a bone conduction hearing device.

21. The hearing device of claim 18, wherein the signal processing system applies amplification that separately compensates for the transmission loss and a hearing loss of a recipient of the hearing device, wherein the hearing prosthesis device is adapted to receive control settings for providing stimulation to the recipient to cause the hearing percept in the user based on the received sound signal such that the hearing percept is based on amplification of the signal from the microphone that separately compensates for the transmission loss and the hearing loss of the recipient of the hearing device, and wherein the hearing device is a middle ear mechanical stimulation system.

22. The method of claim 1, wherein the transmission loss is at least in part due to transcranial attenuation.

23. The method of claim 1, wherein the transmission loss is at least in part due to attenuation by at least one of skin or a skull of the recipient.

24. The fitting system of claim 7, wherein the fitting system is configured to receive input indicative of a type of hearing loss and a type of connection between a bone conduction device and the recipient, and to at least one of calculate the transmission loss based in part on that input or generate the one or more control settings in part on that input.

25. The fitting system of claim 7, herein the fitting system is configured to receive input indicative of pressure management features of the hearing prosthesis, and to at least one of calculate the transmission loss based in part on that input or generate the one or more control settings in part on that input.

26. The method of claim 1, wherein the obtained threshold levels indicative of minimum signal for the hearing device are different from any audiogram data associated with the obtained threshold levels for the recipient unaided by the hearing device.

27. The method of claim 10, wherein a portion of the gain compensates more for the transmission loss than for the hearing loss.

28. The method of claim 10, wherein a portion of the gain compensates for at least about 100% of the transmission loss and compensates for less than half of the hearing loss.

29. The method of claim 1, further comprising determining a hearing loss of the recipient as opposed to the calculated transmission loss for the recipient.

* * * * *